United States Patent [19]

Sumino et al.

[11] Patent Number: 4,511,984

[45] Date of Patent: Apr. 16, 1985

[54] ULTRASOUND DIAGNOSTIC APPARATUS

[75] Inventors: Yoichi Sumino; Susumu Enjoji, both of Ootawara, Japan

[73] Assignee: Tokyo Shibaura Denki Kabushiki Kaisha, Kawasaki, Japan

[21] Appl. No.: 411,310

[22] Filed: Aug. 25, 1982

[30] Foreign Application Priority Data

Sep. 19, 1981 [JP] Japan ................. 56-147018

[51] Int. Cl.³ ............................................. G06F 15/42
[52] U.S. Cl. ..................................... 364/415; 73/602; 128/660
[58] Field of Search ............... 364/413, 414, 415, 417, 364/576; 73/602, 606, 614, 620, 625, 626; 128/660, 661, 662, 663

[56] References Cited

U.S. PATENT DOCUMENTS

| | | | |
|---|---|---|---|
| 4,063,549 | 12/1977 | Beretsky et al. | 364/415 X |
| 4,361,043 | 11/1982 | Engle | 128/660 X |
| 4,375,671 | 3/1983 | Engle | 364/414 X |
| 4,409,838 | 10/1983 | Schomberg | 128/660 X |

OTHER PUBLICATIONS

IEEE Transactions on Biomedical Engineering, vol. BME-27, No. 6, Jun. 1980, "Clinical Application of an Ultrasound Attenation Coefficient Estimation Technique for Liver Pathology Characterization"; by: Roman Kuc.

*Primary Examiner*—Errol A. Krass
*Assistant Examiner*—Edward R. Cosimano
*Attorney, Agent, or Firm*—Oblon, Fisher, Spivak, McClelland & Maier

[57] ABSTRACT

An ultrasound diagnostic apparatus for use in the imaging or characterization of biological tissue, including an ultrasonic probe, a gate circuit, a spectrum analysis device, a computation device and a display. The ultrasonic probe emits ultrasonic beams and receives the reflected echo signals from tissue interfaces. The reflected signals are sampled by the gate circuit and are Fourier-analyzed by the spectrum analysis device, and then the computation device derives frequency-dependant ultrasonic attenuation properties therefrom. The results of the computation device are displayed by the display to indicate the state of the tissue.

17 Claims, 9 Drawing Figures

ULTRASOUND DIAGNOSTIC APPARATUS

BACKGROUND OF THE INVENTION

1. Field of the Invention:

This invention relates to an ultrasonic diagnostic apparatus for use in the imaging or characterization of biological tissue.

2. Description of the Prior Art:

Ultrasonic imaging systems are at present well known. The most widely used technique is the pulse echo B-Scan mode, or variants thereof, in which a video display employs intensity modulation to depict echo return amplitude as a function of depth.

The echoes are generated at interfaces between media of different acoustic impedance within the specimen tissue. However, the magnitude of the interfacial reflection coefficient depends not only on the impedance ratio, but also on the angle of incidence of the beam, and furthermore the echo amplitude is reduced due to attenuation from the intervening tissue. Thus, the images generated by B-Scan systems illustrate the geometry of the interfaces, which can be interpreted qualitatively but do not give quantitative information on bulk tissue due to geometric distortion of the echo amplitude arising from refraction, specular reflection, and diffraction. Therefore, it is difficult to distinguish between tissue states.

Currently in medical diagnostic ultrasound equipment, measurements of the sound speed, attenuation and backscattering are made to assist the clinician by increasing the accuracy and subtlety by which it is possible to differentiate structure and/or function in a particular region of the human body.

Particularly, general information on measurement of the acoustic attenuation coefficient is given in a magazine article entitled "Estimating the Acoustic Attenuation Coefficient Slope for Liver from Reflected Ultrasound Signals" in IEEE Transaction on Sonics and Ultrasonics, Sept. 1979, Vol. SU-26, No. 5, pp. 353–362.

SUMMARY OF THE INVENTION

Accordingly, one object of this invention is to provide a novel ultrasound diagnostic apparatus which can obtain quantitative information from ultrasonic signals reflected on the human body.

Another object of this invention is to provide an ultrasound diagnostic apparatus which can obtain frequency-dependent ultrasonic attenuation properties by frequency-domain analysis.

A further object of this invention is to provide an ultrasound diagnostic apparatus which can obtain a frequency-attenuation slope from the reflected signals selected through regions of interest on a conventional B-mode image by means of signal processing techniques.

These and other objects are achieved according to the invention by providing a novel ultrasound diagnostic apparatus for use in the imaging or characterization of biological tissue, including ultrasonic probe means for emitting ultrasonic beams and for receiving reflected echo signals; pulser means connected to the ultrasonic probe means for initiating generation and emission of an ultrasonic beams by the probe means; gate means coupled to the ultrasonic probe means for sampling echo signals corresponding to predetermined periods in the ultrasonic beams; spectrum analysis means coupled to the gate means for obtaining spectra corresponding to the sampled echo signals by means of Fourier analysis; computation means coupled to the spectrum analysis means for calculating frequency-dependent ultrasonic attenuation properties from the spectra; and display means connected to the computation means for displaying the attenuation properties calculated by the computation means.

DESCRIPTION OF THE PREFERRED EMBODIMENTS

Figure 1:
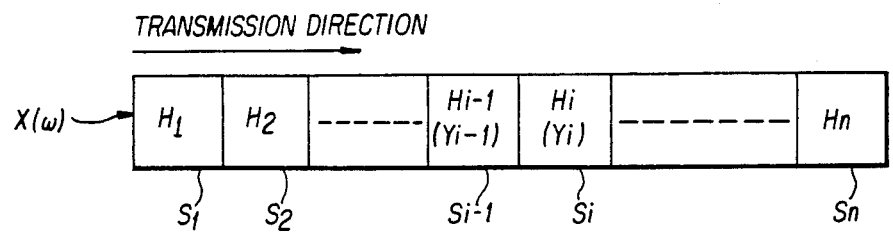
FIG. 1 is an illustration of a tissue model useful to obtain a transfer function, a value of acoustical attenuation and an acoustical attenuation coefficient for each tissue segment using an equal distance segment partitioning technique.

Referring now to the drawings, wherein like reference numerals designate identical or corresponding parts throughout the several views, and more particularly to FIGS. 1, 2 and 3 thereof, a principle to implement estimation of the acoustic attentuation, denoted by a, and the acoustic attenuation coefficient, denoted by b, from the reflected signals will be described.

Generally, the acoustic attentuation, and the amplitude of the reflection is known to increase linearly with frequency.

FIG. 1 is a tissue model having a series of underlying segments (S1-Sn) in the path of an acoustic beam.

The transfer function of each segment in consideration of the effect of the acoustic reflection from tissue interface, acoustic scattering, acoustic absorption, and acoustic attenuation is denoted by $Hn(\omega)$.

An acoustic pulse having an arbitrary spectrum $X(\omega)$ propagates into the tissue model indicated in FIG. 1 and the reflections from the segment Si (i=1, 2, 3, ... n) have a spectrum denoted by $Yi(\omega)$.

Figure 2:
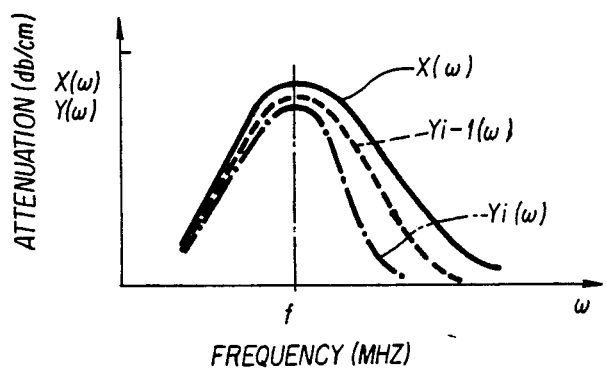
FIG. 2 is a graph showing the slope of the propagating pulse spectrum at different tissue locations obtained from segments in FIG. 1.
Figure 3:
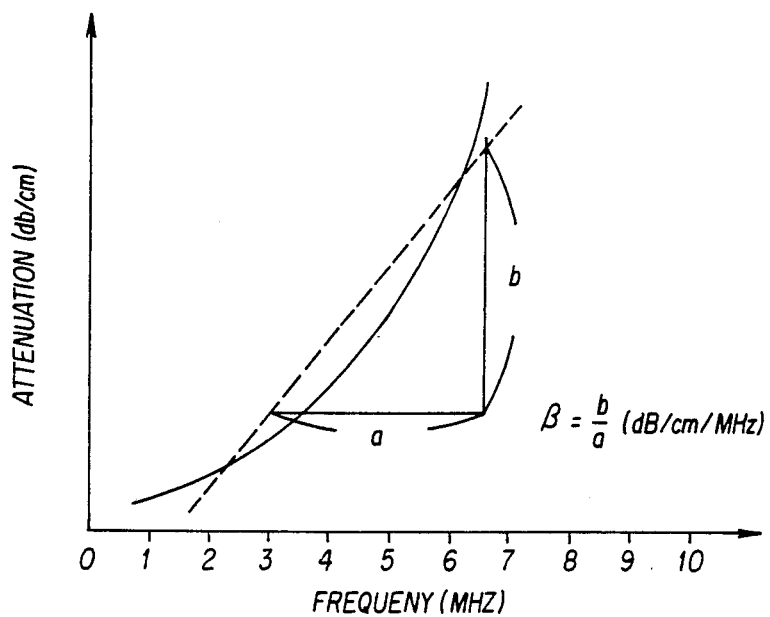
FIG. 3 is a diagram useful in explaining the estimation of the acoustical attenuation coefficient.

The slopes of the propagating pulse spectrum at different tissue locations obtained from these segments are shown in FIG. 2.

The transfer function denoted by $Hi(\omega)$ corresponding to the i th segment is denoted by Si, is calculated from the spectrums of the reflections and is then given by $$Hi(\omega) = Yi(\omega)/Yi-1(\omega) \tag{1}$$

Since we set $$Hi(\omega) = 10^{-a(\omega) \cdot 2x} \tag{2}$$

where x is the acoustical path length through the tissue.

The value of acoustical attenuatin per unit length, denoted by $\alpha(\omega)$, in units of dB/cm is given by $$\alpha(\omega)=(\tfrac{1}{2}x)\log[Yi-1(\omega)/Yi(\omega)]=-(\tfrac{1}{2}x)\log Hi(\omega) \quad (3)$$

This acoustical attenuation is known to increase with frequency.

Nextly calculated are the differences between the sample spectra to estimate the value for a linearly frequency dependent acoustic attenuation denoted by $\beta$.

The coefficient $\beta$ is estimated by fitting a straight line to the spectral difference.

$\beta$ is given by $$\beta = \alpha(\omega)/f \text{ (dB/cm/MHZ)} \quad (4)$$

where $$f = \omega/2\pi$$

The parameter $\beta$ is the important indicator of the state of the tissue.

Figure 4:
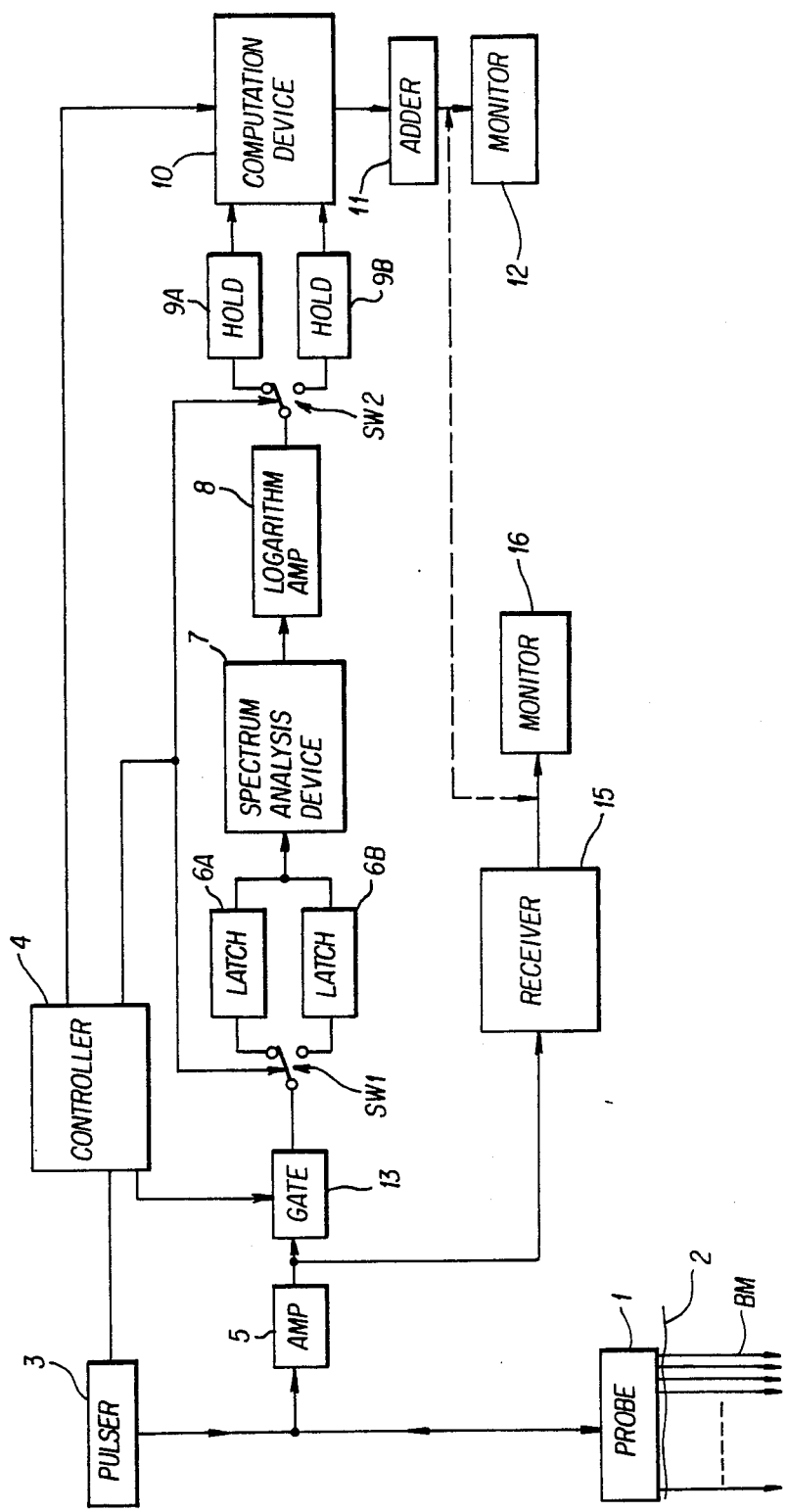
FIG. 4 is a simplified block diagram of the ultrasound diagnositic apparatus according to the present invention.

The basic components of an ultrasound diagnostic apparatus for use in the imaging or characterization of biological tissue are depicted in simplified diagrammatic form in FIG. 4.

The ultrasound diagnostic apparatus includes an ultrasonic probe 1 which is constituted, for example, by 64 electro-mechanical elements such a piezoelectric elements arranged in line.

A pulser 3 applies an ultrasonic pulse to the probe 1 to initiate an ultrasonic beam emission from the probe 1. Probe 1 emits an ultrasonic beam BM which propagates through the tissue 2, and receives an echo signal from a tissue interface. The pulser 3 is under the control of a controller 4 which signals the pulser 3 to produce a start electrical pulse to initiate generation of an acoustic pulse.

The probe 1 is connected via a preamplifier 5 to a receiver 15, which generates signals for displaying an ultrasonic cross-sectional image. The output of the receiver 15 is viewed on a monitor 16 in a video display employing intensity modulation to depict echo return amplitude as a function of depth.

A gate circuit 13 receives the output signals of the preamplifier 5 to sample echo signals corresponding to the predetermined segments Si, Si−1 in the ultrasonic beam path BM. The controller 4 supplies a timing signal to the gate circuit 13 to execute this sampling procedure. The gate 13 is connected to a common terminal of a switch SW1 which is constituted by, for example, an electronic switch element. Both contact of the switch SW1 are connected to latch circuits 6A and 6B, respectively. The echo signal supplied alternatively from the switch SW1 is held in the each latch circuit 6A or 6B, and then led to a spectrum analysis device 7 where it is Fourier-analyzed to obtain a power spectrum corresponding to each segment Si, Si−1. A logarithm amplifier 8 receives the power spectra provided as the outputs of the spectrum analysis device 7 to read out a log spectral log Yi−1 ($\omega$), log Yi($\omega$) via a switch SW2 to hold circuits 9A, 9B.

The logarithm amplifier 8 is connected to a common terminal of the switch SW2 which is constituted by, for example, an electronic switch element. The opposed contacts of the switch SW2 are connected to respective hold circuits 9A and 9B. The log spectral log Yi−($\omega$), log Yi($\omega$) held in each hold circuit 9A, 9B is supplied to a computation device 10 where the log spectral log Yi−1($\omega$) is subtracted from the log spectral log Yi($\omega$). The transfer function Hi($\omega$) given in equation (1) can be written $$\log Hi(\omega) = \log Yi(\omega) - \log Yi-1(\omega) \quad (5)$$

The output of the computation device 10 is applied to an adder 11 to execute an addition manipulation along the ultrasonic beam path for all ultrasonic beams and obtain $\alpha(\omega)$ given in equation (3), and then compute $\delta$ given in equation (4). The parameter is displayed on another monitor 12. This manipulation of the computation device 10 is also initiated by a signal of the controller 4.

If Fast Fourier Transformation hardware operating at a 15 $\mu$s per sample has been used as the Spectrum Analysis device 7, the computation for the transfer function through an entire B-mode tomogram requires 6-7 seconds. Furthermore, a large memory, for example, having 400 kbytes memory capacity, is required to store the reflection data prior to the gate circuit 13. Reduction of through-put time for the Fourier analysis and rendering the large memory unnecessary is achieved by a selection device 14 in FIG. 5.

Figure 5:
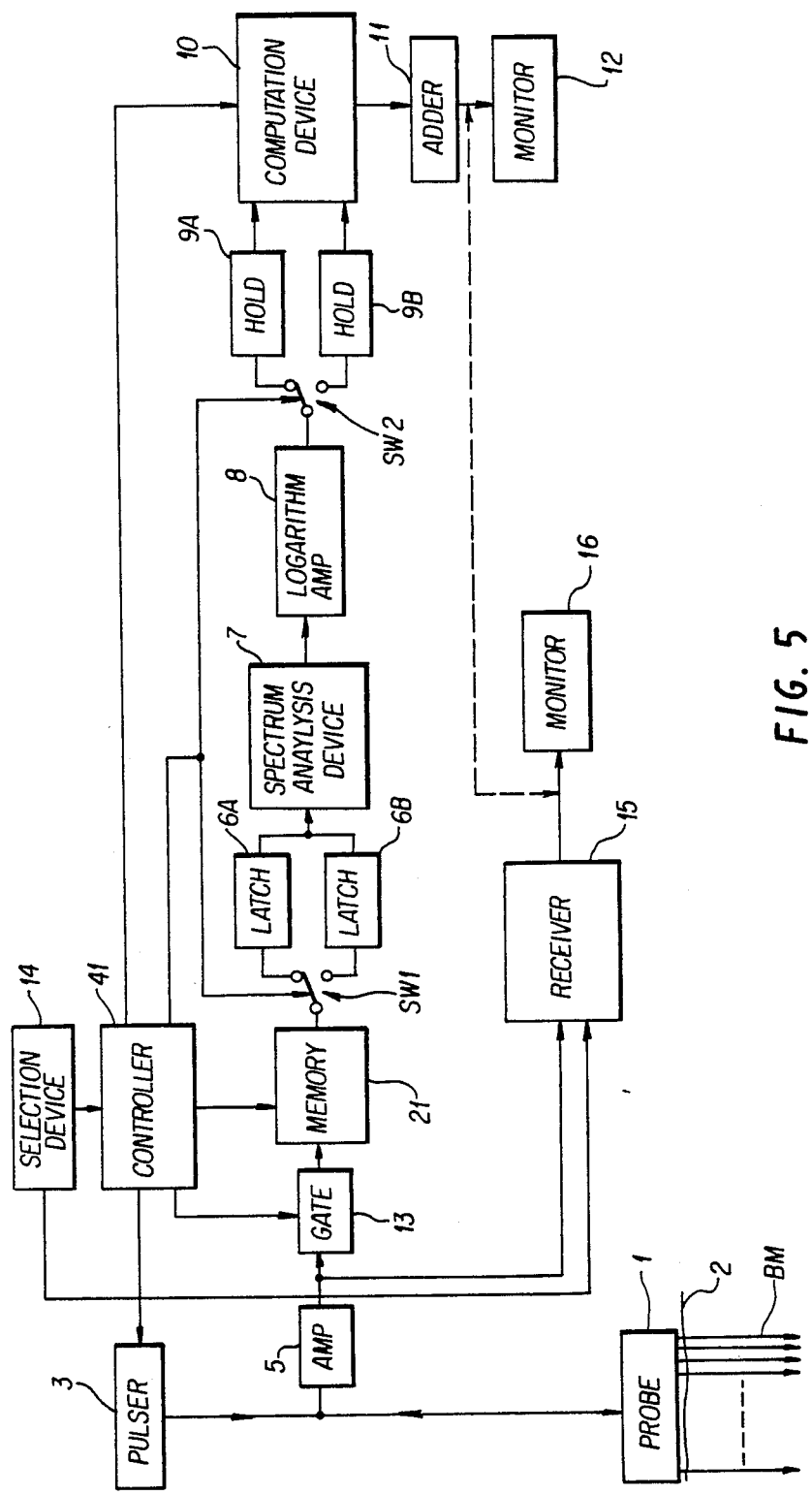
FIG. 5 is a simplified block diagram of another embodiment of the ultrasound diagnostic apparatus employing a selectin device in the embodiment shown in FIG. 4.
Figure 6:
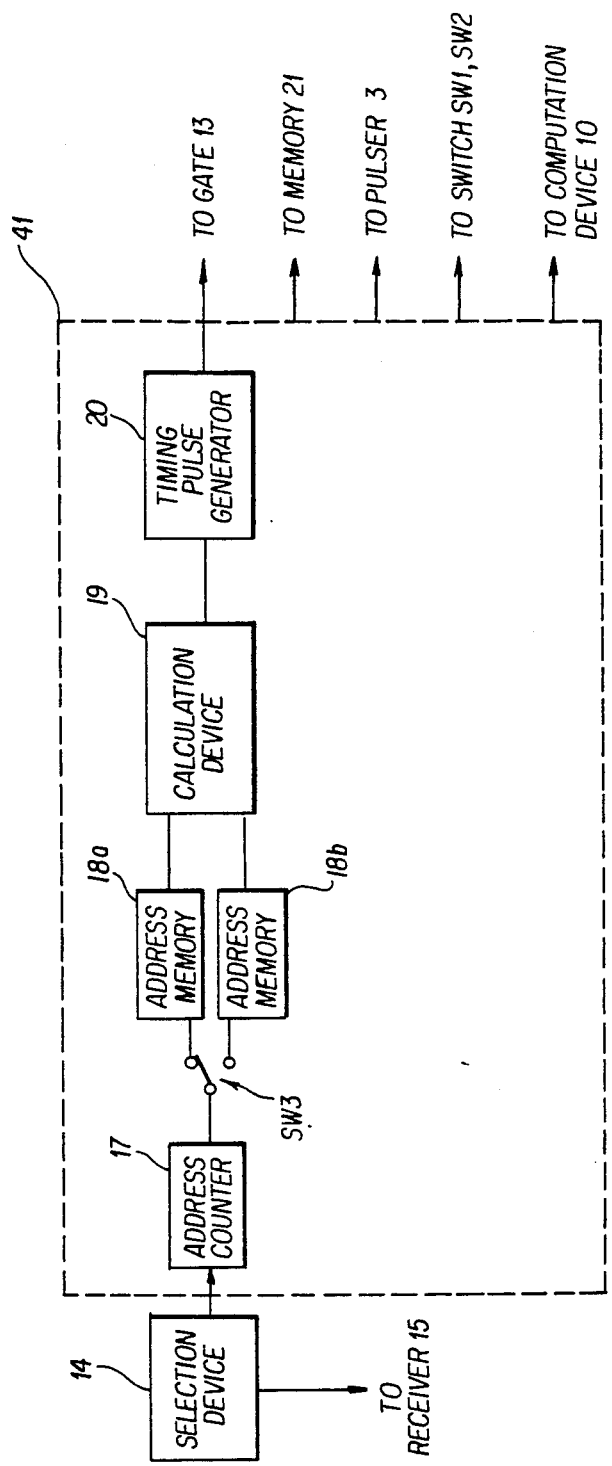
FIG. 6 is a detailed block diagram of the selection device and the controller shown in FIG. 5.

Referring to FIG. 5, which illustrates a second embodiment of the invention, the sampling period of the gate circuit 13 of the ultrasonic beam selected through regions of interest on a conventional B-mode tomogram can be set by the selection device 14 connected to the controller 41. The probe 1 is coupled to a preamplifier 5 where it is amplified. The output signals of the preamplifier 5 are supplied to the receiver 15 and the gate circuit 13, respectively. The selection device 14, which includes, for example, a joystick, is connected to the receiver 15 and the controller 14, respectively. As shown in FIG. 6, the controller 41 includes an address counter 17 which is connected to a common terminal of a switch SW3, a pair of address memories 18a and 18b to which both contacts of the switch SW3 are connected respectively, an address calculation device 19 and a timing pulse generator 20 which is connected to the gate circuit 13.

The echo data which have been obtained by the probe 1, for a B-mode tomogram are assigned to picture elements or pixels in a coordinate system encompassing the regions of interest. Markers corresponding to A-mode waveforms selected by the selection device 14 are superimposed on a conventional B-mode tomogram on the monitor 16. The addresses in each pixel defined by the markers are designated from the address counter 17. The address of one edge position of the marker is led via the switch SW3 to the address memory 18a to be stored, and the address of the other edge position of the markers is led via the switch SW3 to the address memory 18b to be stored. The addresses of all pixels of the markers are supplied with the calculated results to the timing pulse generator 20. The output of the timing pulse generator 20 is led to the gate circuit 13 for giving the sampling period corresponding to each address from the address calculation device 19. Both the phase and the amplitude of waveforms selected are stored in a memory 21 which is connected to the gate circuit 13. The memory 21 has a capacity at least able to store the echo data on the markers.

The output of the memory 21 is supplied to the latch circuits 6A and 6B via the switch SW1 for processing as previously explained.

If the computation time of the Fourier transformer is a value within the interval of the transmission pulses from the probe 1, the memory 21 is not required.

The display by the ultrasound diagnostic apparatus is described and explained with reference to FIGS. 7a, 7b, and 7c.

Figure 7C:
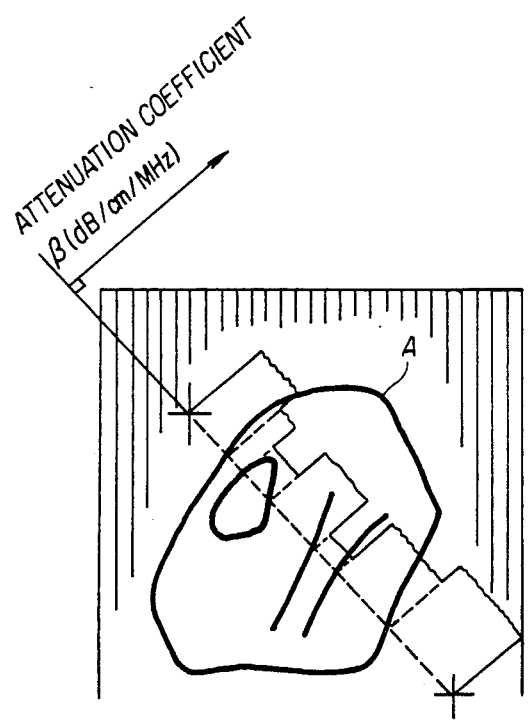
FIGS. 7a, 7b, 7c are illustrations of respective techniques of displaying frequency-dependent ultrasonic attenuation properties according to the present invention.
Figure 7A:
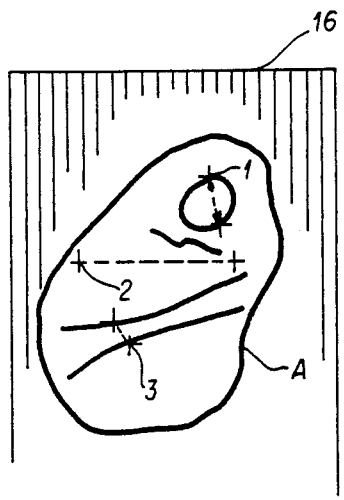

In FIG. 7a, three regions of interest on a conventional B-mode tomogram A are indicated by three sets of marker denoted by (1), (2) and (3), on the monitor 16.

Figure 7B:
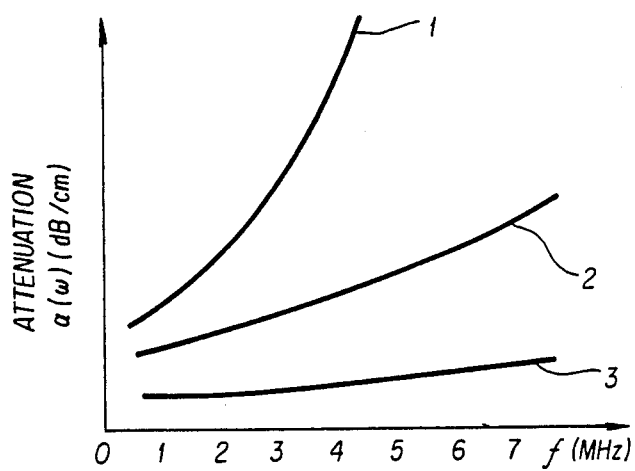

The slopes of acoustical attenuation per unit length, denoted by $\alpha(\omega)$, on A-mode waveforms defined by each marker are displayed on the other monitor 12 as shown in FIG. 7b.

In FIG. 7c, the acoustical attenuation coefficients $\beta$ calculated by the computation device 10 along the A-mode waveforms selected by the selection device 14 are superimposed on a conventional B-mode tomogram A.

Also, the slopes of acoustical attenuation per unit length, denoted by $\alpha(\omega)$, and a conventional B-mode tomogram A can be displayed on the same monitor.

In summary an ultrasound diagnostic apparatus is described which measures and computes a constitutively significant parameter of soft biological tissue. The ultrasound diagnostic apparatus can obtain Frequency-dependent ultrasonic attenuation properties and represent these properties visually.

By the ultrasound diagnostic apparatus, the indicators of the state of the human tissue are visualized.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An ultrasonic diagnostic apparatus for use in evaluating characteristics of a subject, comprising:
    ultrasonic probe means for transmitting ultrasonic beams having predetermined frequency spectra and for receiving reflected echo signals, said probe means scanning said subject in a predetermined cross sectional plane wth the transmitted ultrasonic beams;
    pulser means connected to said ultrasonic probe means for initiating generation and transmission of ultrasonic beams by said probe means;
    gate means coupled to said ultrasonic probe means for sampling reflected echo signals at predetermined sampling time periods after transmission of said ultrasonic beams by said probe means to divide said echo signals into predetermined segments corresponding to successive incremental time periods;
    spectrum analysis means coupled to said gate means for obtaining frequency spectra of the echo signals of each of said segments by means of Fourier analysis;
    processing means coupled to said spectrum analysis means for determining a transfer function associated with each of said segments as a function of differences between the frequency spectra of successive segments and for deriving at least one frequency-dependent ultrasonic attentuation parameter based on the transfer functions associated with plural of said segments; and,
    controlling means coupled to said pulser means, and said processing means for controlling the generation and scanning of said ultrasonic beams, the sampling by said gate means, and the determining of said at least one parameter by said processing means.

2. An ultrasonic diagnostic apparatus according to claim 1, wherein said processing means comprises:
    adder means for adding the successively determined transfer functions of plural said successive segments to produce an attenuation parameter $\alpha(\omega)$ characteristic of attenuation as a function of frequency of portions of said subject corresponding to said plural successive segments.

3. An ultrasonic diagnostic apparatus according to claim 2, wherein said processing means comprises:
    means for deriving an attenuation parameter $\beta$ indicative of the state of the subject based on a straight line fitted on the attenuation parameter $\alpha(\omega)$.

4. An ultrasonic diagnostic apparatus according to claim 1, comprising:
    receiver means coupled to said ultrasonic probe means for receiving an ultrasonic cross-sectional image and for producing intensity modulation display signals indicative of echo return amplitude as a function of depth;
    first display means coupled to said receiver means for displaying said cross-sectional image;
    selection means coupled to said controller means and said receiver means for setting the sampling time periods corresponding to said echo signal segments based on the cross-sectional image displayed by said first display means; and
    second display means connected to said processing means for displaying at least one of said at least one parameters determined by said processing means.

5. An ultrasonic diagnostic apparatus according to claim 1, comprising:
    latch means connected between said gate means and said spectrum analyser means for latching the echo signal sampled by said gate means;
    hold means connected between said spectrum analysis means and said processing means for holding the spectra associated with said successive segments as obtained by said spectrum analysis means; and
    said processing means comprising,
    means for determining the difference between the spectra of said successive segments held by said hold means to derive the transfer function associated with each of said successive segments, and
    means for adding the transfer functions associated with plural of said segments to derive an attenuation parameter $\alpha(\omega)$ indicative of attenuation as a function of frequency of a portion of said subject associated with said plural segments.

6. An ultrasonic diagnostic apparatus according to claim 5, wherein said processing means further comprises:
    means for deriving a coefficient $\beta$ determined by fitting a straight line to said attenuation parameter $\alpha(\omega)$.

7. An ultrasonic diagnostic apparatus according to claim 1, wherein said ultrasonic probe means comprises:
    a plurality of ultrasonic transducers which are excited periodically by said pulser means.

8. An ultrasonic diagnostic apparatus according to claim 7, comprising:

memory means coupled to said gate means and controlled by said controlling means for storing the echo date sampled by said gate means for each said sampling period.

9. An ultrasonic diagnostic apparatus according to claim 4, wherein said controller means comprises:
   address counter means for designating addresses corresponding to opposed edges of an A-mode wave form selected by said selection means;
   a pair of address memories for storing said addresses designated by said address counter means;
   calculation means for determining sampling periods based on said stored addresses; and
   timing pulse generator means for supplying timing pulses corresponding to said sampling period.

10. An ultrasonic diagnostic apparatus according to claim 9, wherein said processing means comprises:
    adder means for adding the successively determined transfer functions of plural said successive segments to produce an attenuation parameter $\alpha(\omega)$ characteristic of attenuation as a function of frequency of portions of said subject corresponding to said plural successive segments.

11. An ultrasonic diagnostic apparatus according to claim 10, wherein said processing means comprises:
    means for deriving an attenuation parameter $\beta$ indicative of the state of the subject based on a straight line fitted on the attenuation parameter $\alpha(\omega)$.

12. An ultrasonic diagnostic apparatus according to claim 2, comprising:
    receiver means coupled to said ultrasonic probe means for receiving an ultrasonic cross-sectional image and for producing intensity modulation display signals indicative of echo return amplitude as a function of depth;
    first display means coupled to said receiver means for displaying said cross-sectional image;
    selection means coupled to said controller means and said receiver means for setting the sampling time periods corresponding to said echo signal segments based on the cross-sectional image displayed by said first display means; and
    second display means connected to said processing means for displaying at least one of said at least one parameters determined by said processing means.

13. An ultrasonic diagnostic apparatus according to claim 9, comprising:
    latch means connected between said gate means and said spectrum analyser means for latching the echo signal sampled by said gate means;
    hold means connected between said spectrum analysis means and said processing means for holding the spectra associated with said successive segments as obtained by said spectrum analysis means; and
    said processing means comprising,
    means for determining the difference between the spectra of said successive segments held by said hold means to derive the transfer function associated with each of said successive segments, and
    means for adding the transfer functions associated with plural of said segments to derive an attenuation parameter $\alpha(\omega)$ indicative of attenuation as a function of frequency of a portion of said subject associated with said plural segments.

14. An ultrasonic diagnostic apparatus according to claim 13, wherein said processing means further comprises:
    means for deriving a coefficient $\beta$ determined by fitting a straight line to said attenuation parameter $\alpha(\omega)$.

15. An ultrasonic diagnostic apparatus according to claim 3, comprising:
    receiver means coupled to said ultrasonic probe means for receiving an ultrasonic cross-sectional image and for producing intensity modulation display signals indicative of echo return amplitude as a function of depth:
    first display means coupled to said receiver means for displaying said cross-sectional image;
    selection means coupled to said controller means and said receiver means for setting the sampling time periods corresponding to said echo signal segments based on the cross-sectional image displayed by said first display means; and
    second display means connected to said processing means for displaying at least one of said at least one parameter determined by said processing means.

16. An ultrasonic diagnostic apparatus according to claim 4, comprising:
    latch means connected between said gate means and said spectrum analyser means for latching the echo signal sampled by said gate means;
    hold means connected between said spectrum analysis means and said processing means for holding the spectra associated with said successive segments as obtained by said spectrum analysis means; and
    said processing means comprising,
    means for determining the difference between the spectra of said successive segments held by said hold means to derive the transfer function associated with each of said successive segments, and
    means for adding the transfer functions associated with plural of said segments to derive an attenuation parameter $\alpha(\omega)$ indicative of attenuation as a function of frequency of a portion of said subject associated with said plural segments.

17. An ultrasonic diagnostic apparatus according to claim 16, wherein said processing means further comprises:
    means for deriving a coefficient $\beta$ determined by fitting a straight line to said attenuation parameter $\alpha(\omega)$.

* * * * *